United States Patent [19]

Weller et al.

[11] Patent Number: 5,046,854

[45] Date of Patent: Sep. 10, 1991

[54] PHOTOMETRIC CELL AND PROBE HAVING WINDOWS FUSION SEALED TO A METALLIC BODY

[75] Inventors: Joseph P. Weller, Lake Jackson; David P. Denton, Richwood; Sandra V. Lange; Chester R. Norman, both of Lake Jackson, all of Tex.; Mary A. Leugers, Midland, Mich.; Stuart Farquharson, Surfside; Jean P. Chauvel, Jr., Lake Jackson, both of Tex.

[73] Assignee: The Dow Chemical Company, Midland, Mich.

[21] Appl. No.: 647,179

[22] Filed: Jan. 24, 1991

Related U.S. Application Data

[63] Continuation of Ser. No. 474,702, Feb. 1, 1990, abandoned, which is a continuation of Ser. No. 149,320, Jan. 28, 1988, abandoned.

[51] Int. Cl.$^5$ .................... G01N 21/05; G01N 21/09
[52] U.S. Cl. .................................. 356/440; 250/576; 356/246
[58] Field of Search ............... 356/409, 410, 440, 442, 356/246; 250/575, 576

[56] References Cited

U.S. PATENT DOCUMENTS

| | | | |
|---|---|---|---|
| 2,964,640 | 12/1960 | Wippler | 356/442 |
| 3,177,706 | 4/1965 | Shuman et al. | 356/440 |
| 3,263,025 | 7/1966 | Wheeler | 174/151 |
| 3,281,174 | 10/1966 | Heil | 287/189.365 |
| 3,281,523 | 10/1966 | Kuehne et al. | 174/50.61 |
| 3,289,291 | 12/1966 | Reed | 29/473.1 |
| 3,323,821 | 6/1967 | Kuehne et al. | 287/189.365 |
| 3,394,451 | 7/1968 | Stuart | 29/473.1 |
| 3,415,556 | 12/1968 | Dryden | 287/189.365 |
| 3,555,450 | 1/1971 | Rockwell, Jr. | 331/94.5 |
| 3,736,650 | 6/1973 | Anderson | 29/473.1 |
| 3,886,364 | 5/1975 | Walker et al. | 250/343 |
| 3,969,126 | 7/1976 | Anderson | 106/290 |
| 4,063,803 | 12/1977 | Wright et al. | 350/319 |
| 4,064,826 | 12/1977 | Pauli | 116/117 C |
| 4,179,037 | 12/1979 | Chan et al. | 220/2.3 R |
| 4,188,126 | 2/1980 | Boisde et al. | 356/440 |
| 4,355,321 | 10/1982 | Yeats | 357/30 |
| 4,577,110 | 3/1986 | MacBride et al. | 356/417 X |
| 4,614,428 | 9/1986 | Harris et al. | 356/246 |
| 4,666,251 | 5/1987 | Liberman et al. | 350/319 |
| 4,682,846 | 7/1987 | Cowen | 350/96.18 |
| 4,707,134 | 11/1987 | McLachlan et al. | 356/342 |

FOREIGN PATENT DOCUMENTS 206433  12/1986  European Pat. Off. ............ 356/409

OTHER PUBLICATIONS

Eimac Division of Varian Associates Sales Brochure, Jan., 1984.
H. Burnham Tinker and Donald E. Morris, "High Pressure, High Temperature Infrared-Ultraviolet-Visible Spectrophotometer Cell for in situ Catalyst Studies", The Review of Scientific Instruments, vol. 43, No. 7, Jul. 1972, pp. 1024-1026.
K. Noack, "An Infrared High-Pressure Cell", Spectrochimica Acta, vol. 24A, 1968, pp. 1917-1920.
Johannes M. L. Penninger, "A Spectroscopic Flow Reactor for In Situ Studies of Heterogeneous Catalysts at Elevated Pressure and Temperature by Means of IR Transmission Spectroscopy", Journal of Catalysis, vol. 56, 1979, pp. 287-289.
C. S. Fong, J. V. Fox, C. E. Mauk and H. W. Prengle, Jr., "Equipment for High-Pressure Infrared Measurements", Applied Spectroscopy, vol. 24, No. 1, 1970, pp. 21-27.
Thomas Papanek and Thomas L. Fabry, "A High Pressure Optical Cell for Study of Biochemical Solutions", The Review of Scientific Instruments, vol. 43, No. 5, May 1972, pp. 738-739.
VWR Scientific Catalog, 1984-1985, p. 1470.

Primary Examiner—Vincent P. McGraw
Attorney, Agent, or Firm—Timothy S. Stevens

[57] ABSTRACT

A photometric probe or a photometric cell having separate windows and a metallic probe body or cell body. The window(s) are sealed to the probe or cell body by brazed or frit seals which are less likely to leak after extended use in high temperature and/or high pressure industrial applications than probes and cells having gasket sealed windows. The windows can be made of sapphire, cubic zirconia, diamond, ruby, glass or quartz and, in the case of the probe, can be in the shape of an Attenuated Total Reflectance prism. The probe or cell body can be Kovar alloy or stainless steel.

2 Claims, 1 Drawing Sheet

PHOTOMETRIC CELL AND PROBE HAVING WINDOWS FUSION SEALED TO A METALLIC BODY

This is a continuation of application Ser. No. 07/474,702, filed Feb. 1, 1990, now abandoned, which is a continuation of application Ser. No. 07/149,320, filed Jan. 28, 1988, now abandoned.

FIELD OF THE INVENTION

The invention is in the field of photometric analysis systems and more specifically in the field of cells and probes used in photometric analysis systems.

BACKGROUND OF THE INVENTION

Most photometric analyses are made using a cell or probe to isolate a sample to be analyzed from a light source and a photodetector. In the case of a cell, the cell body contains a cavity in which the sample is placed and the body comprises two windows so that light from the source can be passed through one of the windows, through the sample, through the other window and then to the photodetector. The cell can be made entirely of a material transparent to the light, e.g., a test tube, or can be made with separate windows mounted and sealed to a cell body and even separate windows mounted and sealed to a metallic body. One advantage of a cell having separate windows and a metallic body is that it can be built to withstand higher sample temperature and pressure, e.g., a cell connected to a high pressure and/or high temperature chemical process so that a fluid sample stream from the process can be passed through the cavity of the cell and photometrically analyzed, e.g., the high pressure infrared cell of Walker et al. U.S. Pat. No. 3,886,364.

Conventional cells of the Walker et al. type employ a gasket material between the windows and the metallic cell body (or between the windows and removable metallic window mounts which are removable from the cell body to facilitate replacement of the windows). Many advancements have been made in gasket sealing such windows to reduce the problem of sample leaking between the windows and the metallic cell body (or between the windows and the metallic window mounts) for high temperature and/or high pressure applications. See, for example, Papanek et al., *The Review of Scientific Instruments*, May, 1972, page 738-739; Tinker et al., *The Review of Scientific Instruments*, July, 1972, pages 1024-1026; Noack, *Spectrochimica Acta*, Vol. 24A, 1968, pages 1917-1920; Penninger, *Journal of Catalysis*, 56, 1979, pages 287-289; and Fong et al., *Applied Spectroscopy*, Vol. 24, Number 1, 1970, pages 21-27. One problem the conventional cells still have is a tendency to leak after extended usage, e.g., as the gaskets deteriorate. This can cause the windows to fog with leaked sample on the side of the window opposite the sample side which can interfere with the accuracy of analysis. Worse yet, some leaks can result in damage to other parts of the photometric analysis system and if the leak is severe can even cause an industrial accident.

In the case of a probe used in photometric analysis, a window is generally mounted and sealed at an end of a metallic hollow tube-shaped body. The window end of the probe can be immersed into a sample while light is directed through the window into the sample and then, sometimes after bouncing off a mirror and sometimes after bouncing off a particle in the sample, back through the window to a photodetector. The light is often directed from the source to the probe and then from the probe to the photodetector by optical fibers. The window can be a prism for Attenuated Total Reflectance (ATR) analysis of the sample. The probe can be mounted in a high pressure and/or high temperature chemical process line or reactor, e.g., the fiber optic probe of McLachlan et al U.S. Pat. No. 4,707,134.

Conventional probes of the McLachlan et al. type employ a gasket material between the window and the metallic probe body. One problem of these conventional probes is a tendency to leak after extended usage in high temperature and/or high pressure industrial applications, e.g., as the gaskets deteriorate, with the same deleterious results as noted above with gasket sealed windows in photometric cells.

Sealing a window to metallic bodies using a brazed seal is known. Chan et al. U.S. Pat. No. 4,179,037 describes a xenon arc lamp having a sapphire window, a Kovar alloy body and a brazed seal between the window and the body. Rockwell U.S. Pat. No. 3,555,450 describes a laser having a quartz window, a metal window mount and a brazed seal between the window and the window mount. U.S. Pat. Nos. 3,281,174, 3,289,291, 3,323,821, 3,415,556, 3,736,650, 3,281,523 and 3,969,126 (all assigned to Varian Associates of Palo Alto, Calif.) teach many aspects of brazed seals. The aforementioned publications and patents are fully incorporated herein by reference. The Eimac Division of Varian Associates sells sapphire and other windows brazed to metallic bodies including sapphire windows brazed near the end of a short tube.

Sealing a window to bodies using a frit seal is known. Liberman et al. U.S. Pat. No. 4,666,251 describes a metal vapor Raman cell having very large windows using a frit seal. Wright et al. U.S. Pat. No. 4,063,803 describes a laser having a window sealed to the laser tube using a frit seal. Sinclair Manufacturing, Inc. of Chartley, Mass., sells sapphire and other windows frit sealed to metal bodies. Fusion sealing windows to ceramic cell bodies (such as quartz windows to quartz cell bodies) is well known for atmospheric pressure photometric cells.

SUMMARY OF THE INVENTION

The present invention is a solution to the above-stated problem of leakage past a gasket sealed window with the use of photometric cells and probes having metallic bodies in high pressure and/or high temperature industrial applications. The solution is to use a window that is fusion sealed, e.g., braze sealed or frit sealed, to the metallic body of a photometric probe or to the metallic body of a photometric cell (or to a metallic demountable portion of the body of a photometric cell).

In one embodiment, the invention is a nonleaking probe system suitable for high temperature and/or high pressure industrial applications. This embodiment comprises a window having a first side and a second side (such as a sapphire window having flat sides or a window shaped like a prism), a metallic probe body (such as a metal tube having a flange or threaded portion for mounting the probe in a pipe or a chemical reactor), a light source (such as an electric lamp, glow bar or light emitting diode), a photodetector (such as a photodiode detector), a continuous fused seal between the window and the metallic body (such as a frit seal or a brazed seal), means for directing light from the source to the first side of the window (such as an optical fiber, one or more lenses, one or more mirrors), and means for directing light from the first side of the window to the photodetector (such as an optical fiber, one or more lenses, one or more mirrors). This structure is used so that light from the source can be passed to and through the window into a sample positioned on the second side of the window and then, after, for example, bouncing off of a mirror or a particle in the sample, passed back through the window to the photodetector essentially without any of the sample leaking between the window and the metallic body of the probe.

In another embodiment, the invention is a nonleaking photometric cell suitable for high temperature and/or high pressure industrial applications. This embodiment comprises a first window, a second window, a metallic body defining a cavity therein, the metallic body having at least a first aperture and a second aperture each in communication with the cavity (such as a high pressure tubing cross made of stainless steel), the first window positioned at the first aperture, the second window positioned at the second aperture, a first continuous fused seal between the metallic body adjacent the first aperture and the first window (such as a brazed seal between the window and a demountable portion of the metallic body, e.g., a stainless steel tube having a sapphire window brazed at one end and fixed into one port of a high pressure tubing cross), and a second continuous fused seal between the metallic body adjacent the second aperture and the second window. This structure is used so that light can be passed through the first window into a sample positioned between the two windows in the cavity and then through the second window to a photodetector essentially without any of the sample leaking between the first window and the metallic body or between the second window and the metallic body.

DETAILED DESCRIPTION OF THE INVENTION

Figure 1:
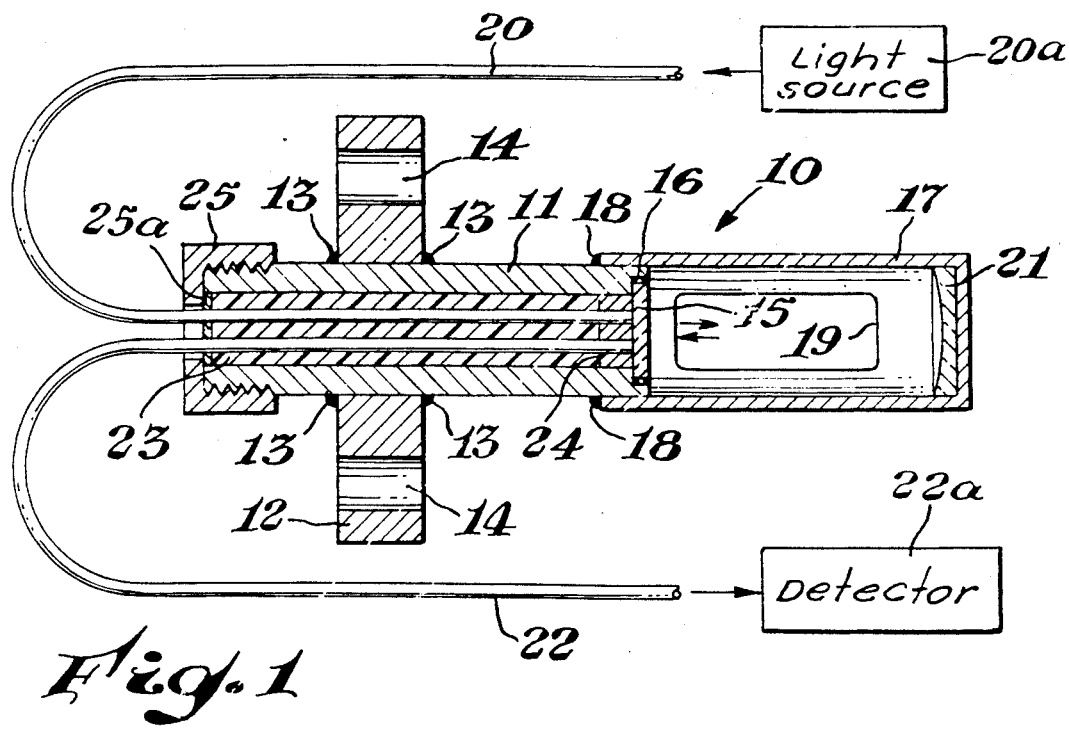
FIG. 1 is a side view, mostly in section and partly in full, of a fiber optic photometric probe embodiment of the present invention showing a window brazed to the metallic body of the probe.

Referring now to FIG. 1, therein is shown a side view of a photometric probe 10. The probe 10 includes a Kovar Alloy tube 11 mounted in a flange 12 by welds 13. The flange 12 contains bolt holes 14 so that the probe 10 can be installed in a high pressure/high temperature chemical process stream or reactor. A sapphire window 15 is shown brazed to the tube 11 by a continuous ring of silver alloy brazing compound 16 so that there are no gaps for leakage between the window 15 and the tube 11. Kovar tubes having sapphire windows brazed at one end are available from the Eimac Division of Varian Associates, supra. The cataloged Eimac assemblies have the sapphire window brazed in a straight tube and not in a step as shown in FIG. 1. The step embodiment shown in FIG. 1 is preferred for high pressure applications. A source of stepped tubes having brazed sapphire windows is Alberox Inc. of New Bedford, Mass. A cap 17 is shown attached to the tube 11 by a weld 18. The weld 18 is preferably made by the electron beam process so as not to affect the integrity of the brazed seal 16. The cap 17 has an opening 19 to allow fluid flow to the interior of the cap 17. The probe 10 is preferably plated with a metal resistant to corrosion from the sample to cover the braze seal 16 if the braze material is attacked by the sample, e.g., plated with nickel for the application of Example 1 below. Light from a Guided Wave Instrument Corporation Model #100-20 Monochromator, shown schematically as a light source 20a, is directed into an optical fiber 20 and passes along the fiber 20, through the window 15 to a curved mirror 21. The light then bounces off of the mirror 21 and then passes through the window 15 and into another optical fiber 22. The light then travels along the optical fiber 22 to a Guided Wave Instrument Corporation Model #DT100-2 Photomultiplier Detector, shown schematically as a detector 22a. The optical fibers 20 and 22 can be the Guided Wave Instrument Corporation's Super Guide G-600 optical fiber cable. The optical fibers 20 and 22 are sealed within the tube 11 by room temperature vulcanized silicone rubber sealant 23 and aligned near the window 15 by a perforated guide disk 24. A cap nut 25 and perforated disk 25a aids in the retention of the sealant 23 in the unlikely event that the window 15 breaks in service. The probe 10 can be used without the cap 17 and mirror 21 as a light scattering probe (not unlike the probe of McLachlan et al., supra) or as a Raman probe. The mirror 21 can be protected from attack by a sample by a brazed window positioned in the cap 17 adjacent the mirror 21.

In FIG. 1 the means for directing the light from the light source 20a to the window 15 is shown as the optical fiber 20 and the means for directing light from the window 15 to the detector 22a is the optical fiber 22. It should be understood that the means for directing the light from the source to the window can alternatively comprise lenses and mirrors or even the mounting of a light source within the probe itself such as a light emitting diode mounted adjacent the window 15. Likewise, it should be understood that the means for directing the light from the window to the detector can alternatively comprise lenses and mirrors or even the mounting of a detector within the probe such as a photodiode detector mounted adjacent the window 15.

The specific material used for the window 15 is not critical to the probe aspect of the present invention as long as the window passes the light from the sight source and can be fusion sealed to the metallic probe body. Examples of window materials believed useful in the present invention in addition to sapphire are cubic zirconia, diamond, Suprasil, Infrasil, ruby, optical glasses and quartz. The window 15 can be an ATR prism for ATR analysis of a sample. The specific material used to fusion seal the window to the metallic probe body is not critical to the probe aspect of the present invention as long as the seal is continuous without gaps which could result in leaking. In addition to brazed seals, it is believed that frit seals are also useful in the probe aspect of the present invention. The specific metal used for the probe body is not critical to the present invention as long as a window can be fusion sealed to the metal. It is believed that the probe body can comprise, in addition to Kovar Alloy and stainless steel, tantalum, Invar Alloy, Monel Alloy, nickel, steel, copper and brass. Kovar Alloy has approximately the same thermal expansion rate as sapphire and is a preferred material. When sapphire windows are brazed to stainless steel, a thin copper washer is usually interpositioned between the window and the stainless steel to lessen the problem of the different rates of thermal expansion of sapphire and stainless steel.

Figure 2:
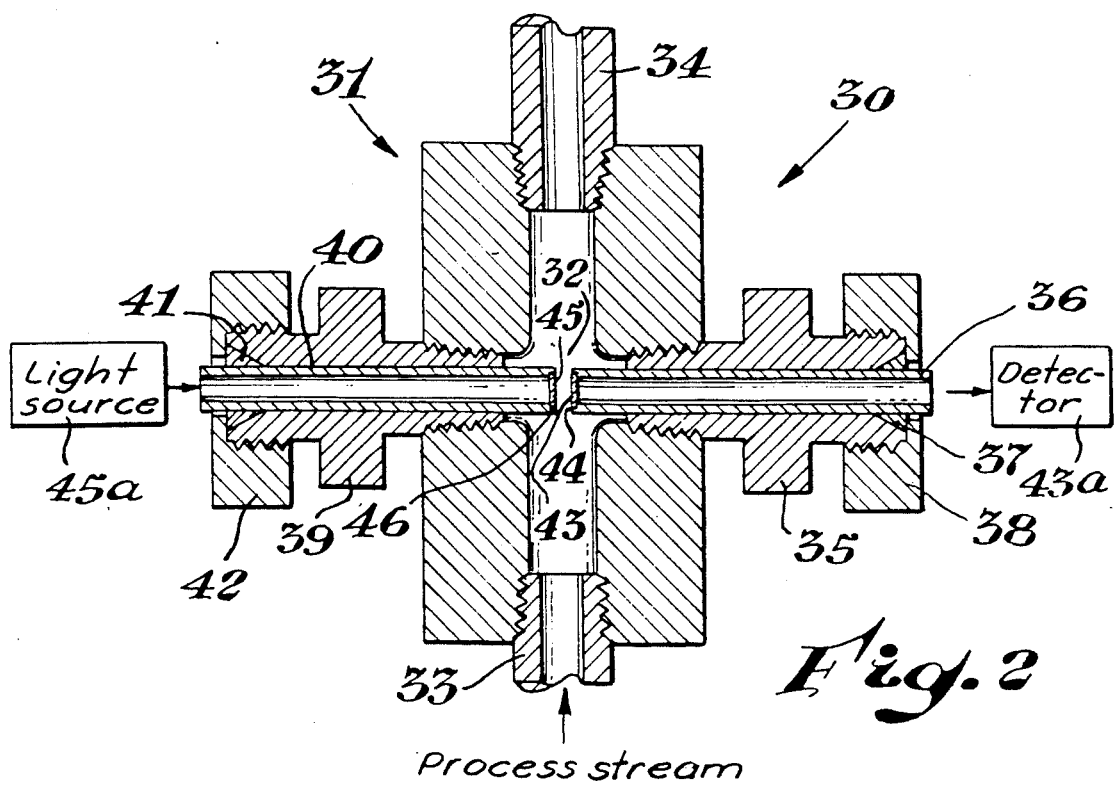
FIG. 2 is a side view, mostly in section and partly in full, of a photometric cell embodiment of the present invention showing windows brazed to demountable metallic tube portions of the cell body.

Referring to FIG. 2, therein is shown a photometric cell embodiment 30 of the present invention. The cell 30 is based on a high pressure stainless steel tubing cross 31 which defines a chamber 32. A pipe 33 is shown threadably connected to the cross 31 so that a fluid process stream can be flowed through the pipe 33 and into the chamber 32. A pipe 34 is shown threadably connected to the cross 31. A tubing connector 35 is shown threadably connected to the cross 31 so that the cell 30 is of the flow through type. A stainless steel tube 36 is shown mounted in the tubing connector 35 by the use of a ferrule 37 and a nut 38. Similarly, a connector 39 is shown threadably attached to the cross 31. A stainless steel tube 40 is shown mounted in the connector 39 by means of a ferrule 41 and a nut 42. A sapphire window 43 is shown brazed to the tube 36 by brazing compound 44. Similarly, a sapphire window 45 is shown brazed to the tube 40 by brazing compound 46. The tube assemblies represented by the reference numerals 36/43/44 and 40/45/46 (obtained by special order from the Eimac Division of Varian Associates, supra) can be adjusted as to the gap between the window 45 and the window 43 so that the path length of the cell 30 can be adjusted as desired. As shown in FIG. 2, the sapphire windows 43 and 45 are brazed into steps in the tubes 36 and 40 so that the windows are more resistant to high pressure in the chamber 32. It should be understood that, in the present invention, the tubes 36 and 40 are considered to be a portion of the cell 30 and fusion sealing a window to them is considered to be the same as fusion sealing a window directly to a cell body. The cell 30 is designed to be placed between a light source 45a and a detector 43a of a photometric analysis system so that a process stream, which is directed through the pipe 33 into the chamber 32 between the windows 45 and 43, can be photometrically analyzed. It should be understood that optical fibers, or any other suitable means, can be used to direct light to and from the cell 30 or that the light source can be placed within the tube 40 and/or that the detector can be placed within the tube 36.

The specific material used for the windows 43 and 45 is not critical in the cell aspect of the present invention as long as the windows pass the light and can be fusion sealed to the metallic cell body (or metallic window mount portions of the cell such as the tubes 36 and 40). Examples of window materials believed useful in the present invention in addition to sapphire are cubic zirconia, diamond, Suprasil, Infrasil, ruby, optical glasses and quartz. The specific material used to fusion seal the windows is not critical in the cell aspect of the present invention as long as the seal is continuous without gaps which could result in leaking. In addition to brazed seals, it is believed that frit seals are also useful in the cell aspect of the present invention. The specific metal used for the cell body is not critical to the present invention as long as a window can be fusion sealed to the metal. It is believed that the probe body can comprise, in addition to Kovar Alloy and stainless steel, tantalum, Invar Alloy, Monel Alloy, nickel, steel, copper and brass. Kovar Alloy has approximately the same thermal expansion rate as sapphire and is a preferred material. When sapphire windows are brazed to stainless steel, a thin copper washer is usually interpositioned between the window and the stainless steel to lessen the problem of the different rates of thermal expansion of sapphire and stainless steel and this was done with the embodiment shown in FIG. 1.

EXAMPLE 1

The system generally shown in FIG. 1 is installed in a chemical process pipeline carrying phosgene so that excess chlorine can be photometrically determined in the phosgene. The monochromator is set at 330 nanometers and full scale response is set at 1,000 ppm chlorine in phosgene. The system shows a lower detection limit of 100 ppm chlorine in phosgene with a noise level of 50 ppm.

EXAMPLE 2

The cell 30 is installed in a polyolefin production plant process stream. The cell 30 is mounted near a Fourier Transform Infrared spectrophotometer using mirrors to direct the infrared light beam from the infrared source through the cell and then to the detector, so that the concentration of olefin monomer can be determined in the process stream.

What is claimed is:

1. A non-leaking photometric cell suitable for high temperature and/or high pressure industrial applications, comprising: a first window; a second window; a first metallic tube; a second metallic tube; a metallic body defining a cavity therein, the metallic body having at least a first aperture and a second aperture thereinto each in communication with the cavity, the first window positioned entirely in the cavity and near an end of the first metallic tube, the first metallic tube being positioned through and removably sealed to the first aperture, the second window positioned entirely in the cavity and near an end of the second metallic tube, the second metallic tube being positioned through and removably sealed to the second aperture; a first continuous brazed seal between the first metallic tube and the first window; and a second continuous brazed seal between the second metallic tube and the second window, so that light can be passed through the first window into a sample positioned between the two windows in the cavity and then through the second window to a photodetector essentially without any of the sample leaking between the first window and the metallic body or between the second window and the metallic body.

2. The cell of claim 1 wherein at least one of the windows comprises a material selected from the group consisting of sapphire, cubic zirconia, diamond, ruby, glass and quartz.

* * * * *